United States Patent [19]
Johnson et al.

[11] Patent Number: 5,662,693
[45] Date of Patent: Sep. 2, 1997

[54] MOBILITY ASSIST FOR THE PARALYZED, AMPUTEED AND SPASTIC PERSON

[75] Inventors: David C. Johnson, Gilford, N.H.; Daniel W. Repperger, Dayton, Ohio

[73] Assignee: The United States of America as represented by the Secretary of the Air Force, Wright-Patterson Air Force Base, Ohio

[21] Appl. No.: 461,085

[22] Filed: Jun. 5, 1995

[51] Int. Cl.⁶ .................................................. A61F 5/00
[52] U.S. Cl. .......................... 607/49; 607/48; 128/782
[58] Field of Search ..................... 607/48, 49; 523/64; 128/782; 602/5, 20, 4, 23, 26

[56] References Cited

U.S. PATENT DOCUMENTS

| | | | |
|---|---|---|---|
| 4,569,352 | 2/1986 | Petrofsky et al. | 607/49 |
| 4,697,808 | 10/1987 | Larson et al. | 607/49 X |
| 4,711,242 | 12/1987 | Petrofsky | 607/49 |
| 4,760,850 | 8/1988 | Phillips et al. | 607/49 |
| 4,783,656 | 11/1988 | Katz et al. | |
| 4,842,607 | 6/1989 | Repperger et al. | |
| 5,101,812 | 4/1992 | Wang | |
| 5,121,747 | 6/1992 | Andrews | |
| 5,252,102 | 10/1993 | Singer et al. | |
| 5,476,441 | 12/1995 | Durfee et al. | 607/49 X |
| 5,482,056 | 1/1996 | Kramer | 128/782 |

*Primary Examiner*—Linda C. Dvorak
*Attorney, Agent, or Firm*—Gina S. Tollefson; Gerald B. Hollins; Thomas L. Kundert

[57] ABSTRACT

Apparatus to actively assist neuromotor disabled to have better leg functional control/use. This system serves as a strength enhancer, support device, and attenuator of spastic motions. The disclosed orthosis is worn on the outside of the leg (or legs) and serves as an active/dynamic brace to prevent leg spasms and other untoward leg motion. It is made of lightweight material such as fiberglass or aluminum and is actuated by pneumatic gas sources which are small, portable, and carried with the device. The device is totally self contained and has no external connection. The system has applicability to patients such as: stroke (cerebral vascular accident), TBI (traumatic brain injury), Muscular Dystrophy, and some spinal cord injured.

2 Claims, 11 Drawing Sheets

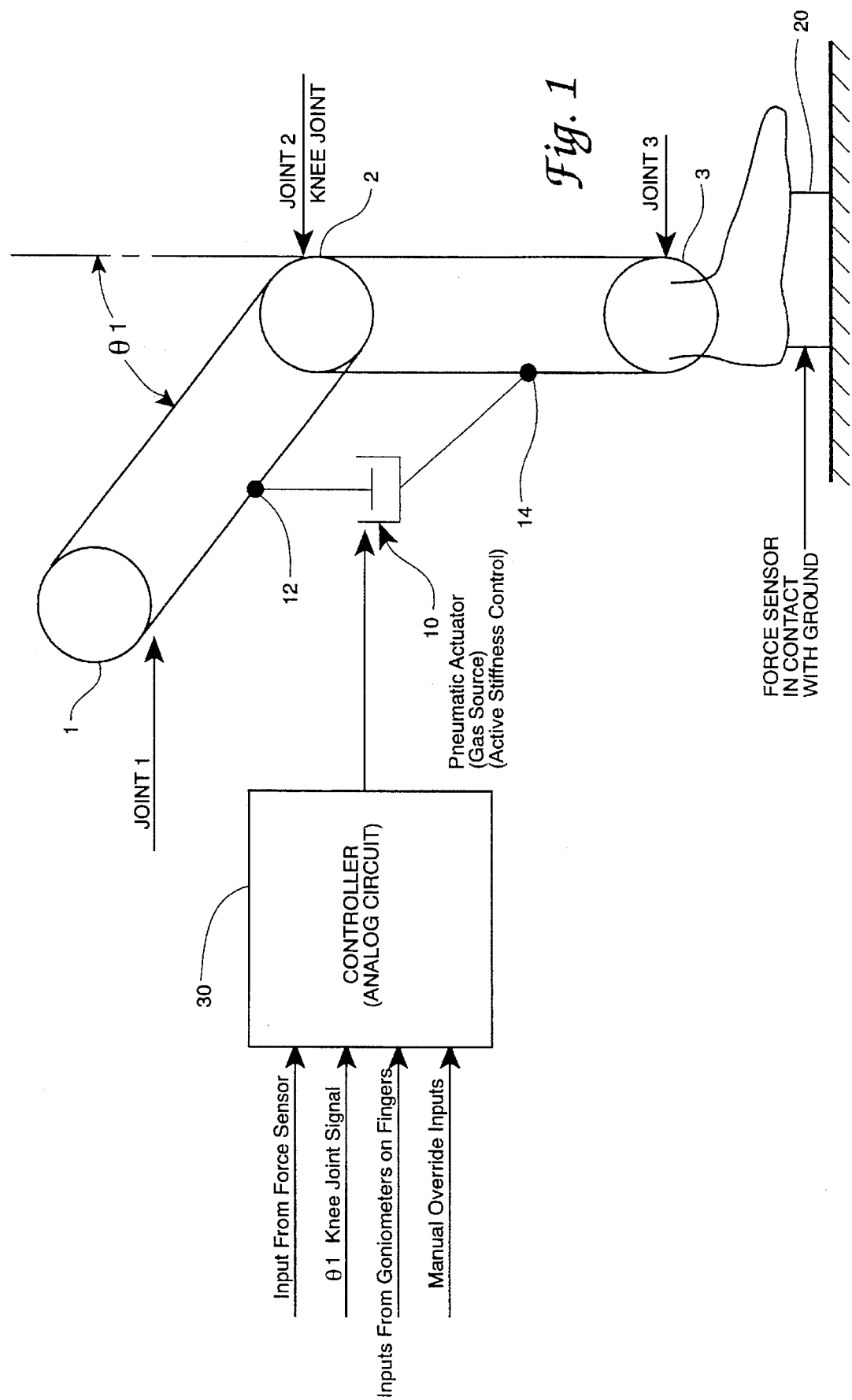

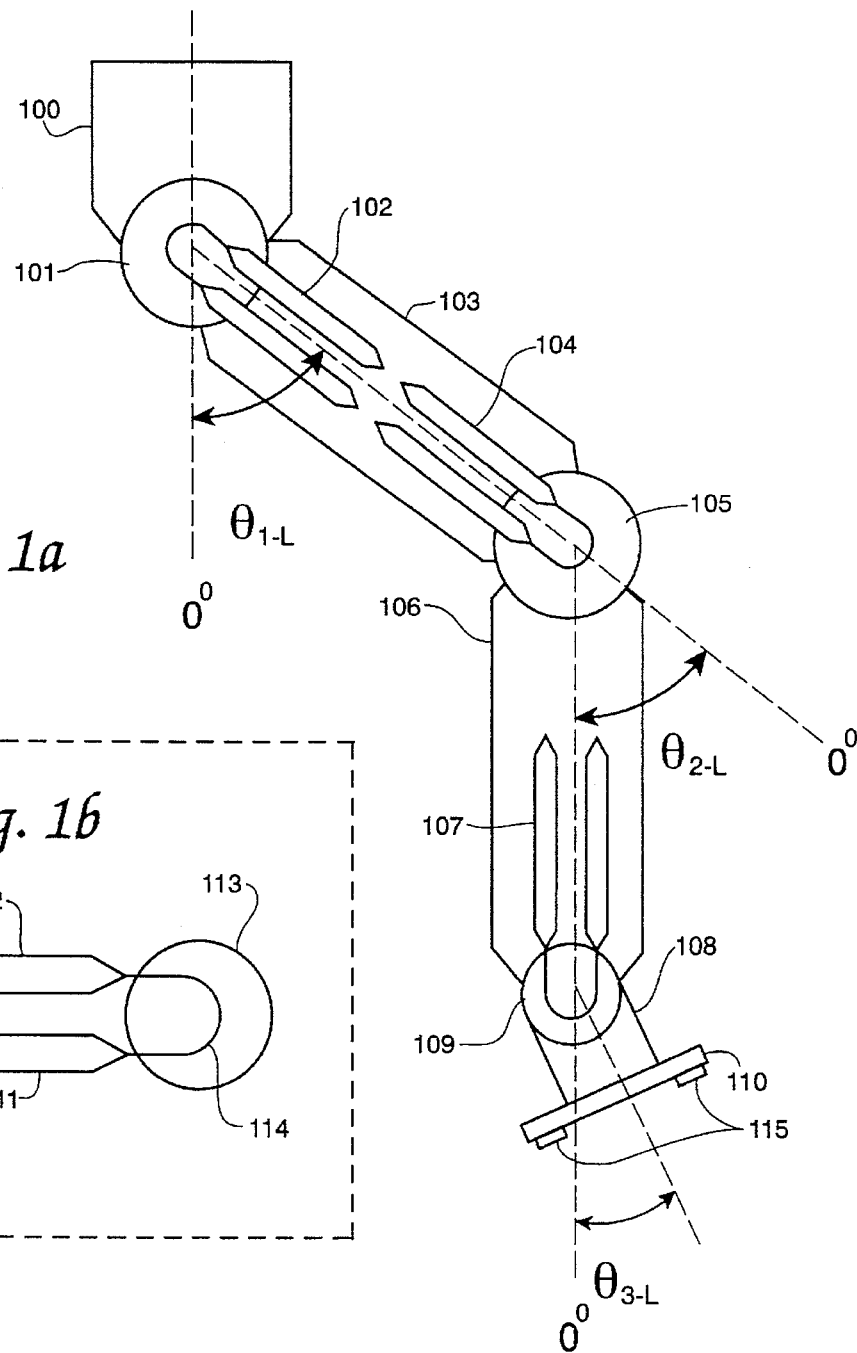

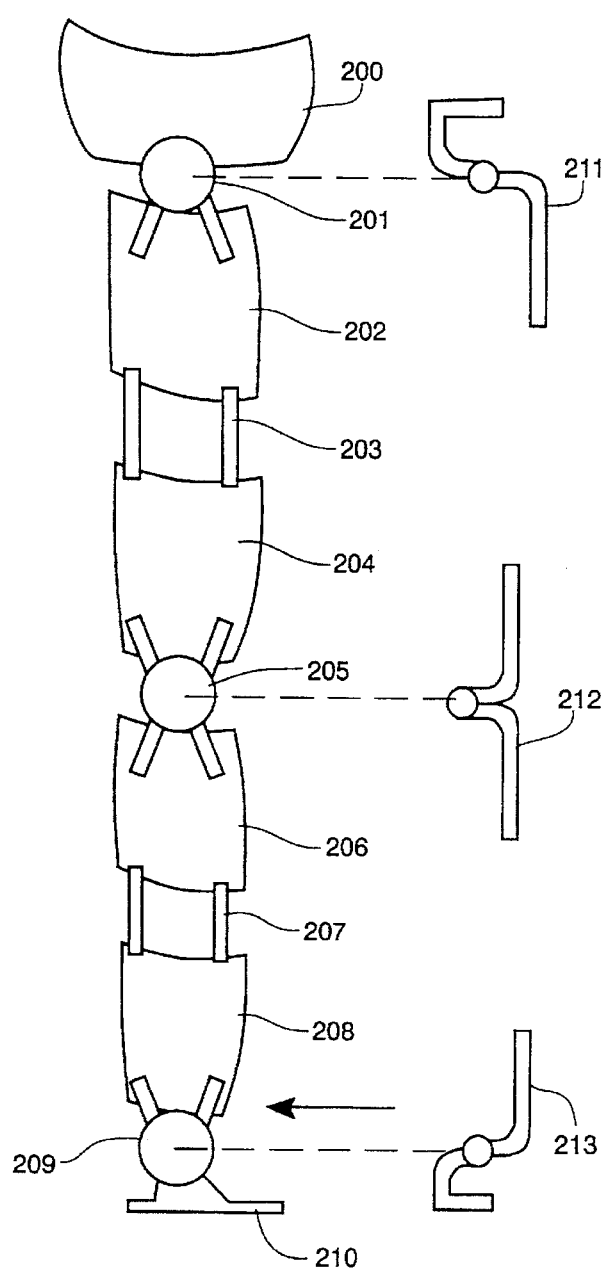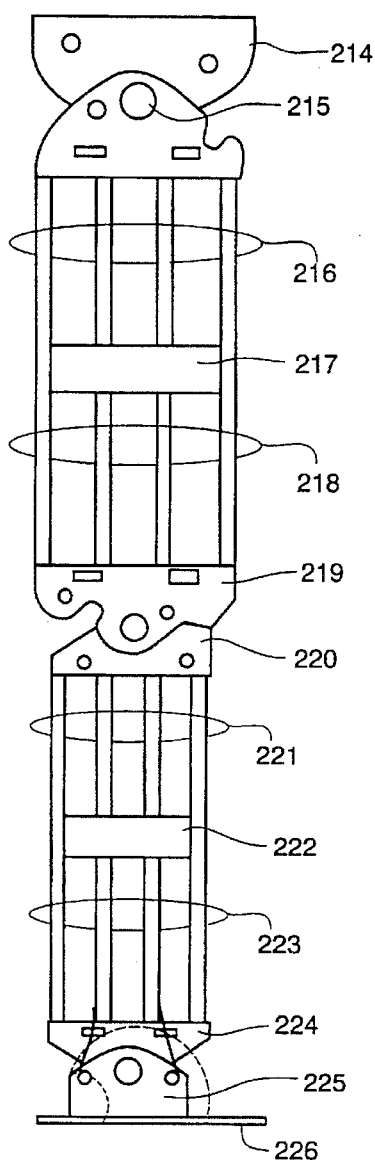
Fig. 2a
Fig. 2b

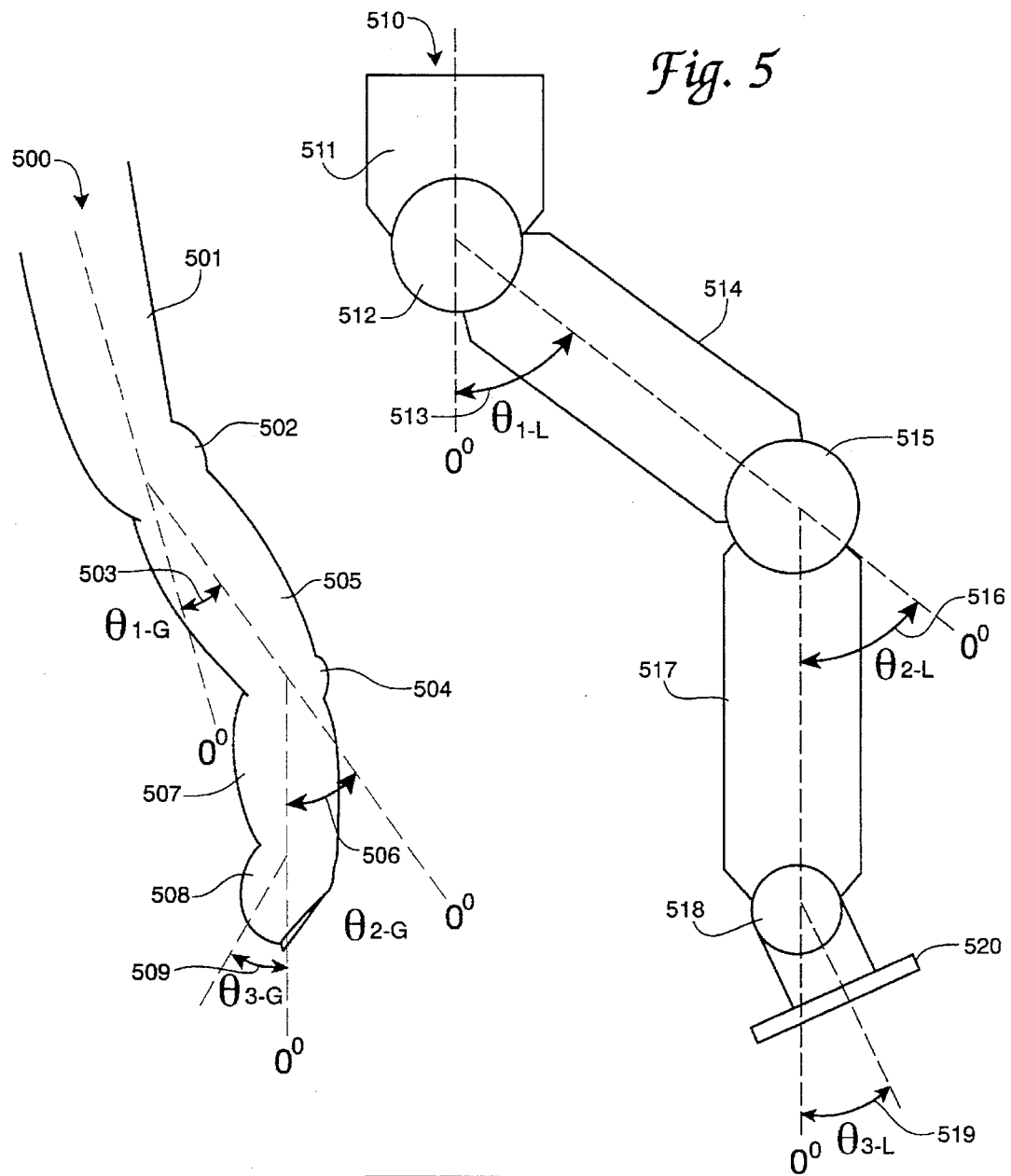

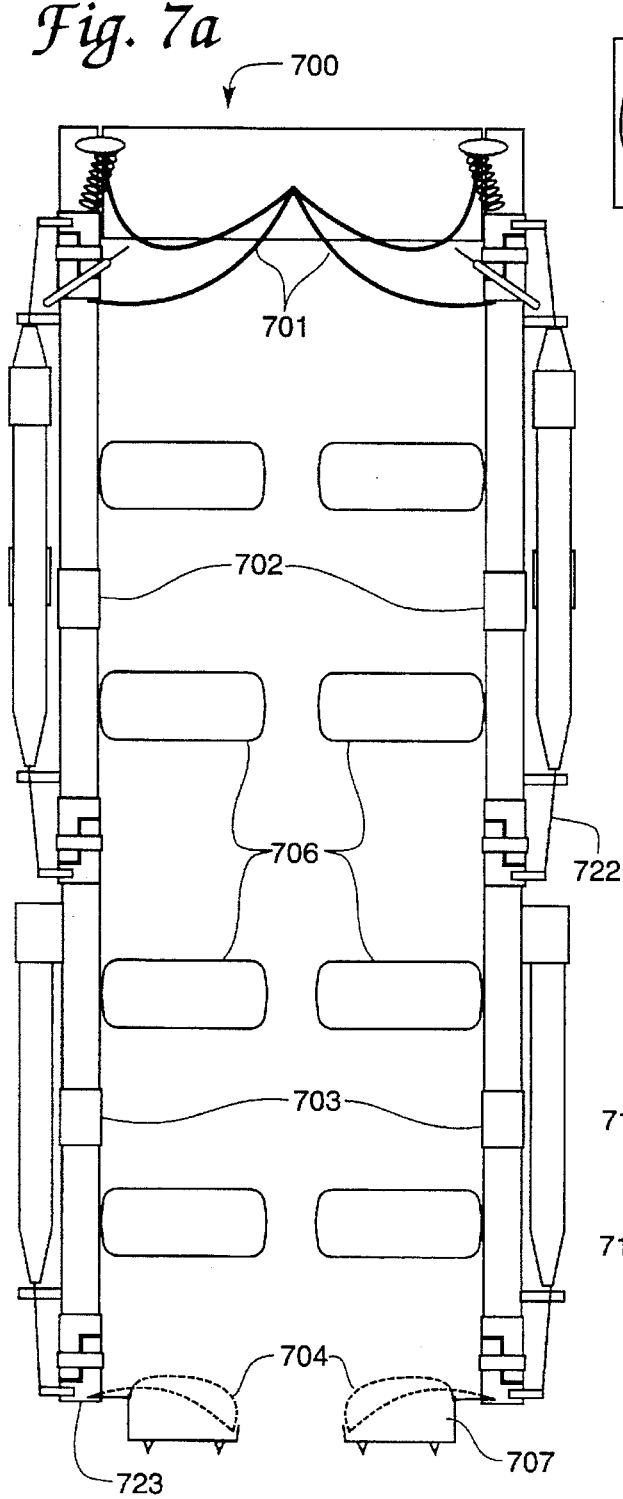
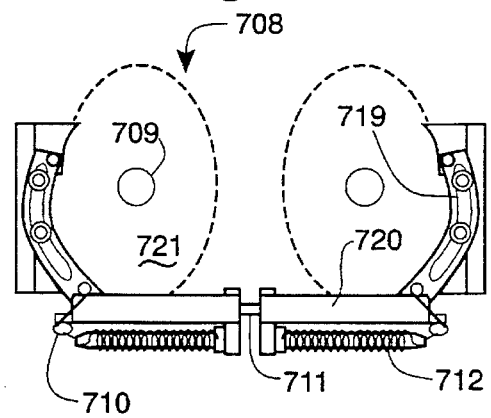
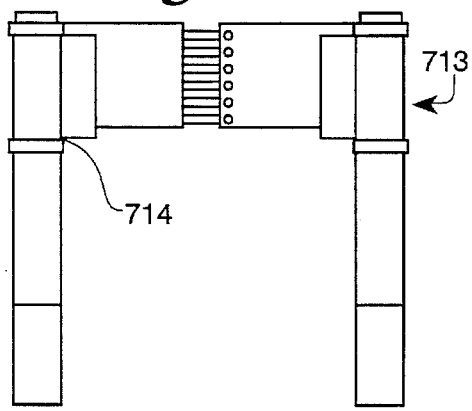
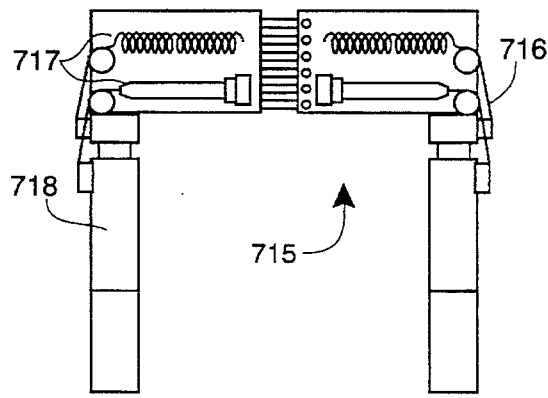

MOBILITY ASSIST FOR THE PARALYZED, AMPUTEED AND SPASTIC PERSON

RIGHTS OF THE GOVERNMENT

The invention described herein may be manufactured ad used by or for the Government of the United States for all governmental purposes without the payment of any royalty.

BACKGROUND OF THE INVENTION

The present invention relates generally to the field of prosthesis apparatus for use in achieving precision movement and overcoming neurological dysfunction movements of a human limb, and more particularly to apparatus for use in achieving mobility assistance for the paralyzed, amputeed, and spastic person (MAPAS).

In the VA system (Department of Veterans Affairs), over 1,000,000 patients are cared for who are confined to wheelchairs for a variety of reasons. In certain diseases (such as stroke), it is extremely important to get the patient on his feet as soon as possible after the disorder reasonably subsides. There are not sufficient physical therapists and facilities to perform this immediate help. With a device as described herein, more patients may be put into physical therapy regimes sooner and thus reduce the long term care necessary for these patients. This device will reduce the amount of manual aid required to administer physical therapy. Also this device provides a method of prodding assistance for those with permanent disabilities who need to walk.

The following references are of interest, and are referenced in the specification.

[1] M. Messner and Asad Davari, "Hydraulically Dampened Knee Flexion Orthosis", The 19th IEEE Annual Northeast Bioengineering Conference, March 18–19, Newark, N.J., pp. 119–120.
[2] K. A. Kacmarek, J. G. Webster, P. Bach-y-Rita, and W. J. Thompkins, "electrotactile and Vibroctile Displays For Sensory Substitution Systems", IEEE Trans. on Biomedical Engineering, Vol. 38, No. 1, January 1991, pp. 1–16.
[3] P. Bach-y-Rita, Brain Mechanisms In Sensory Substitution, New York Academic, 1972.
[4] P. Bach-y-Rita, C. C. Collins, F. A. Saunders, B. White, and L. Scadden, "Vision Substitution By Tactile Image Projection", Nature, Vol. 221, pp. 963–964, 1969.

The following United States patents are of interest.
U.S. Pat. No. 4,842,607 Repperger et al
U.S. Pat. No. 4,783,656 Katz et al
U.S. Pat. No. 5,101,812 Wang
U.S. Pat. No. 5,121,747 Andrews
U.S. Pat. No. 5,252,102 Singer et al.

The Repperger et al. patent utilizes the concept of force reflection to mitigate spastic or tremor movement through the use of a device outside the body. This device, however, is only used on the patient's hand and does not incorporate any outside brace on the leg(s) of the patient.

The Katz patent describes a system for use by quadriplegics and others having less than full use of their limbs for controlling the environment, such as appliances, using a lingually operated switch located on a dental appliance, which activates an FM transmitter.

The Wang patent discloses an orthosis apparatus, which provides support to a user's arms, fingers, and legs.

The Andrews patent describes a functional electrical stimulation orthosis for restoring locomotion in paraplegics. The orthosis comprises knee locking means, sensor means, control means, and, first and second electrode means.

The Singer patent discloses a therapeutic electronic range of motion apparatus which includes a remote subsystem for generating motion commands which are transmitted to a local subsystem at an orthosis, prosthesis or CPM machine.

SUMMARY OF THE INVENTION

An objective of the invention is to provide support and ease of ambulation for a disabled patient using a brace device about the legs.

The invention relates to a device having three features which distinguish it from other devices:

(1) The position and strength of the actuating orthosis muscles are adaptive in the sense that the legs have self stability when it is necessary to support the body weight. This is a consequence of different force or operating characteristics in one direction (when the leg performs an extension) as compared to the reverse motion (contraction). There is a definitive need to have different characteristics in the two directions for the specific application involving people with neuromotor disabilities.

(2) The controller which actuates a portable pneumatic gas source is driven by the patient's fingers in an anthropomorphic manner similar to leg motion. In a sense, the motion of fingers replicates motion that is desired for the legs in the invention.

(3) The patient, using the present invention brace device, has complete control of how stiff his/her legs should be for any force/load. The power required to produce this stiffness is manipulated by the patient.

BRIEF DESCRIPTION OF THE DRAWING

FIG. 1 is a side view diagram of a device according to the invention, with a block showing an analog electronic controller;

FIG. 1a is diagram of an Exoskeleton support or mounting apparatus as seen from the outer side;

FIG. 1b is a diagram of a pneumatic actuator system;

FIG. 2a is a side view of a molded-brace type of support, suggested for use with muscular dystrophy, multiple sclerosis, and rehabilitation patients;

FIG. 2b is a side view of metal brace, suggested for high energy spastic, amputee, paraplegic and quadriplegic patients;

FIG. 5 is diagram showing correlation angles between a sensored hand and the MAPAS assembly;

FIGS. 7a, 7b, 7c & 7d are diagrams comprising front, top front and back views respectively for a detailed description of heavy-duty exoskeleton structure showing attachments of Velcro straps, lower-torso harness assembly, and leg rotation capability;

DETAILED DESCRIPTION

Figure 3A:
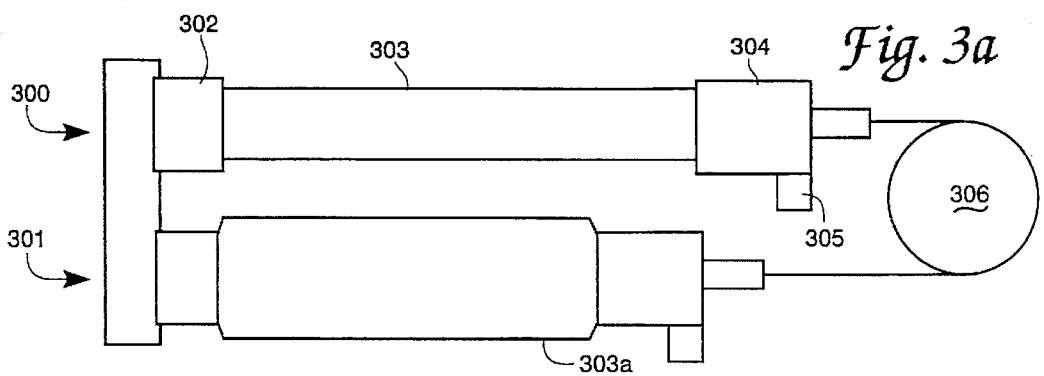
FIG. 3a is diagram showing a pull-pull arrangement of pneumatic muscles.

An objective in the present invention is to provide support and ease of ambulation for a disabled patient using a brace device about one or both legs. This system will help with neuromuscular disorders such as possible leg spasms and other types of neuromotor dysfunction. This device will assist walking for someone who may have a permanent disability and also it can be used in conjunction with a physical therapy regime to reduce the amount of manual assistance required to administer physical therapy.

FIG. 1 illustrates the active orthosis device considered herein, a device which fits individually around one or more legs. The device material is lightweight (preferably it is made of fiberglass or aluminum), and conforms to the leg. An angle $\theta 1$ is defined in FIG. 1 as the knee joint or joint 2 angle, the angle between the thigh and a vertical line. The FIG. 1 links are adjusted so that rotation occurs at the joints 1, 2 and 3. A nonlinear actuator 10 is attached to the link between the thigh at position 12 and the lower leg at position 14. This actuator has the following characteristics based on position, angular rate of change $\dot{\theta}$, and sensed force information:

(i) If $\theta 1 > 0$, and the force measurement is zero (implying that the foot is not in contact with the ground and thus only contracting or extending in normal gait motion), then the force resistance to movement is set to its smallest value.

(ii) If, however, $\theta 1 > 0$, and the force measurement is nonzero (implying that the foot is now in contact with the ground), then the force resistance to movement is set to a large value. With sensing from the position actuator 10 provided, the actuator is arranged to supply force/torque to achieve the proper input angle. The system is now stabilized and the brace will not collapse during support of the body weight of the patient.

(iii) The device can also be locked in place (by manual control and selection).

The reasons why this type of operation is desired is as follows (the preceding parts i–iii are preferably decentralized, i.e. they operate at a loop level at the knee and may not need active interaction by the patient):

(i) If $\dot{\theta} 1 > 0$, and the force sensed is zero then the leg is first contracting or possibly extending. The foot is assumed off the floor and it is desired to have minimum force required to contract and extend the foot. The pneumatic actuator 10 in FIG. 1 can also be used to help perform this option on the leg. It is desired in this phase of the motion to have minimal force of resistance; since the foot is not in contact with the floor, it is required to contract and extend the foot with minimum energy and reactive force.

(ii) If $\dot{\theta} 1 > 0$, and the final extension is almost complete, then it is desired to have a large reactive force. The requirement for the reactive force to be large is that as the foot contacts the floor, the upper body must be stabilized. Empirical studies with actual patients [see ref. 1] have shown that if this force is not sufficiently large when the foot contacts the floor, the device will buckle. This is the main disadvantage of current devices in this area.

(iii) If $\dot{\theta} 1 = 0$, however, it is desired to have the capability of locking the device for stationary operation. This may be required for the patient's standing still or other posture movements where it is desired to just maintain a fixed limb position. This locking mechanism is initiated by manual control by the patient and can be changed at will.

A controller 30 represents an analog logic system which can be used to direct the described operation. Since it is required to have knowledge of whether the foot is in contact with the floor, the logic needs to receive a force measurement (eg. from force sensor 20 a transducer in contact with the ground) to help make the proper decision. In the absence of signals from goniometer sensors a decision rule may be:

If $\dot{\theta} > 0$ and the force sensor or Force Load Cell reads zero,

Then set the reactive force to zero;

or

If $\dot{\theta} > 0$ and the force sensor or Force Load Cell is large,

Then set the reactive force to a large value.

Figure 4:
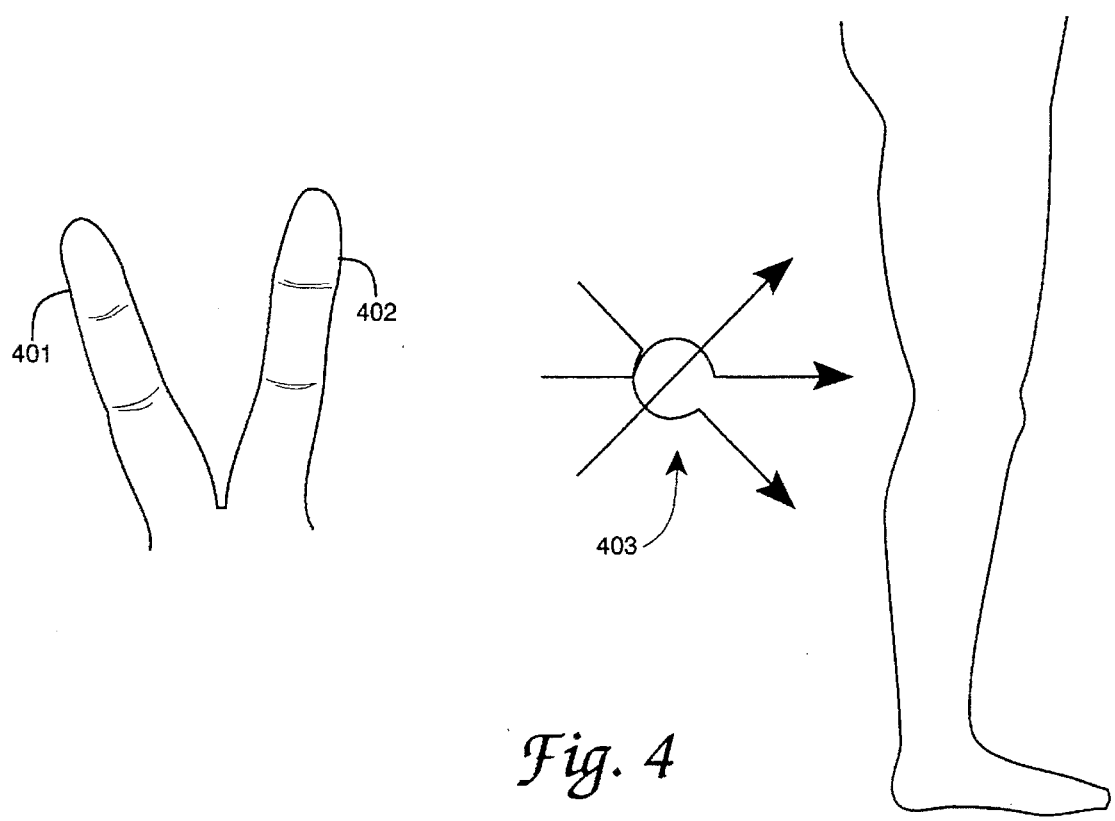
FIG. 4 is a diagram showing the mapping of finger joints directly to the leg joints.

Other rules can be made up with appropriate values of reactive force and the force sensor transducer sensitivity determined from actual tests with patients. FIG. 1a in the drawings shows additional details of an apparatus of the FIG. 1 type. FIG. 1a represents an exoskeleton support or mounting apparatus as seen from the outerside. Four segments include the hip, upper leg, lower leg, and angle assembly with shoe mounting plate. In FIG. 1a the hip segment 100 is attached to a harness which straps to the lower torso around the upper legs and buttocks, the hip joint angle 101 is defined by Theta 1–L where L=leg and provides a standard range of motion of +120 degrees and –30 degrees. Additionally, shown in FIG. 1a are hip joint pneumatic actuator pair 102, upper leg structure 103, and knee joint pneumatic actuator pair 104. We now consider operation of the FIG. 1 apparatus when the loop is not decentralized and is being driven by human input. The goniometer signals to controller 30 now become an important aspect of the system operation. FIG. 4 displays the first two fingers 401 and 402 of the patient, fingers which according to the invention may be used to control leg motion. It is assumed that the patient has good control of these or other fingers. There is in fact a desired mapping (as suggested by the displayed symbol 403) between the links of the fingers 401 and 402 and the respective links of the hip, thigh, and lower leg. This derived mapping is detailed in FIG. 5 of the drawings and a finger 500 is shown hanging (with the thumb cut away) for direct angular comparison. The relationships include the proximal interphalangeal joint 505 mimicking or controlling movement of knee joint 515, the hand segment or metatarsal group 501 controlling movement of hip segment 511, and metatarsal phalangeal joint 502 controlling movement of hip joint 512. According to this relationship, movement of the interphalangeal joint 504 is used to control present system movement of the knee joint 515. Further, the proximal digital segment 505 controls movement of thigh segment 514, interphalangeal segment 507 controls movement of leg segment 517, and distal phalange segment 508 controls movement of ankle/shoe-foot assembly 520. The goniometric measured angles are the metatarsal phalangeal joint angle, or θ1–G, shown at 503, the metatarsal phalangeal joint angle, or θ2–G shown at 506, and the distal interphalangeal joint angle, θ3–G, shown at 509. The relationship of θ1–G to the hip angle is shown at 521, the relationship of θ2–G is shown at 522 and the relationship of θ2–G is shown at 523.

Figure 8A:
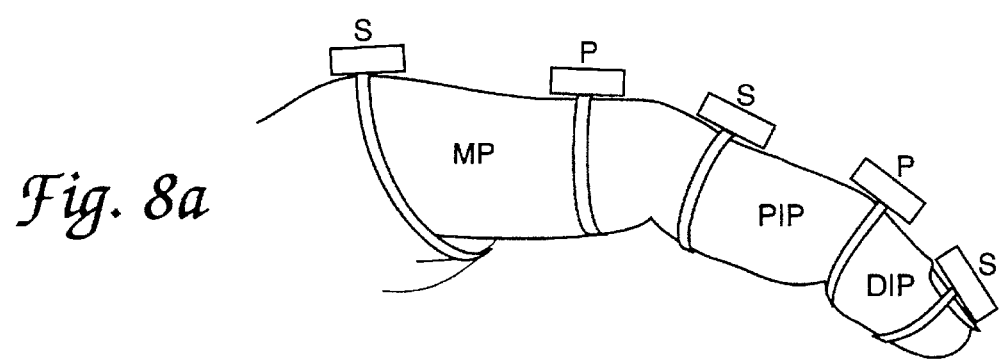
FIGS. 8a and 8b are diagrams showing finger goniometer selection, with FIG. 8a showing a type 1 having primary (field producer) and secondary (sensor coils), and FIG. 8b showing a type 2 having a linear potentiometer with flexible activators.
Figure 8B:
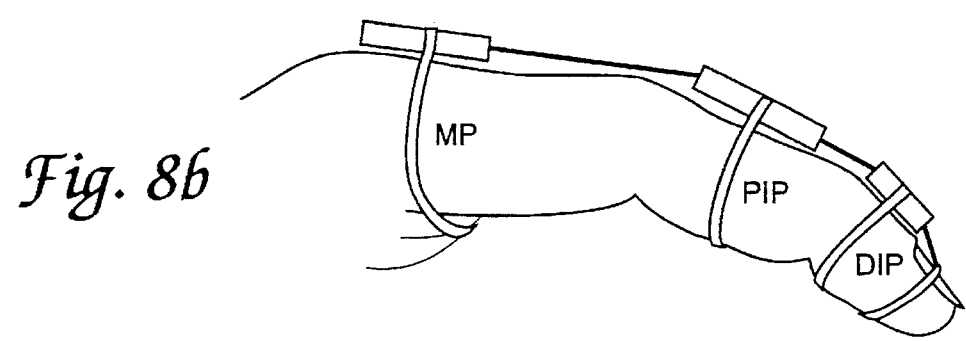
Figure 6A:
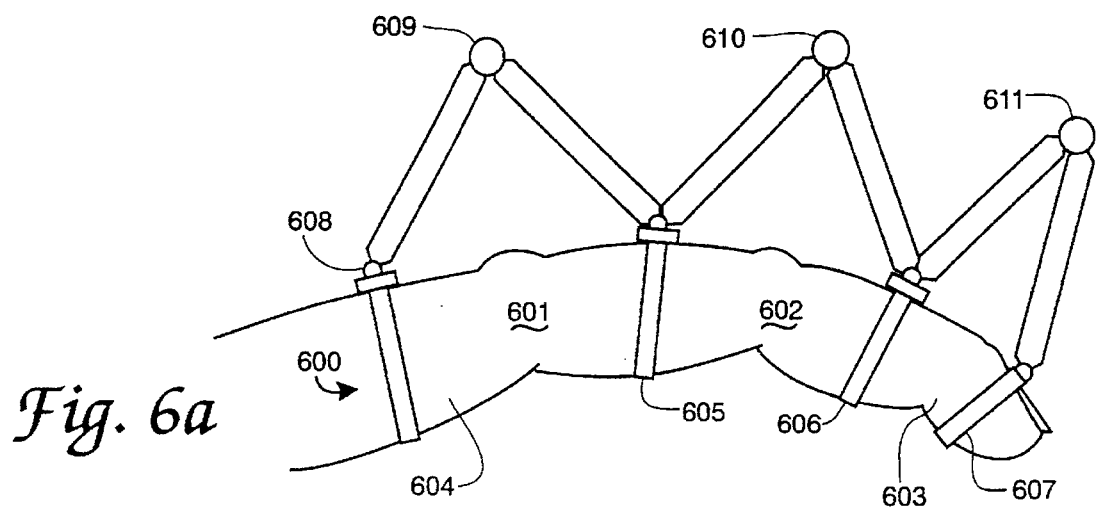
FIG. 6a is a side view of a finger mounted with rotational potentiometer goniometer apparatus.
Figure 6B:
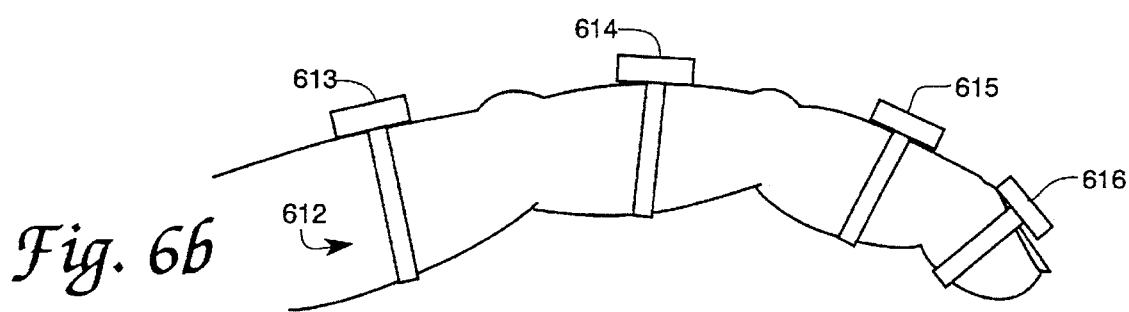
FIG. 6b is a side view of a finger mounted with electromagnetic sensors.

To convert the finger motion to an actuation of the legs, finger goniometers are used. FIGS. 8a and 8b shows two types of goniometers for Finger Goniometer Selections. The first type (FIG. 8a) uses principles from electromagnetic theory to map position changes from the fingers into electrical signals to activate the pneumatic actuators at the joints. In FIG. 8a, by Faraday's Law, changes in orientation cause loss of transmission of magnetic fields which can be transferred to the pneumatic actuator. This type of goniometer is further illustrated in FIG. 6b. FIG. 6b is a side view of a finger mounted with electromagnetic sensors. Segments of the finger are mounted with a first primary sensor 613, a first secondary sensor 614, a second primary sensor 615 and a second secondary sensor 616. The second primary sensor is modulated with respect to the first primary for proper operation. The first secondary sensor 614 picks up magnetic fields from both primaries located on the hand and second digital segment. The fields generated from each of the primaries are coordinated to avoid interfering with each other and this can be accomplished by switching duty cycles in time or having different output frequencies.

Figure 6C:
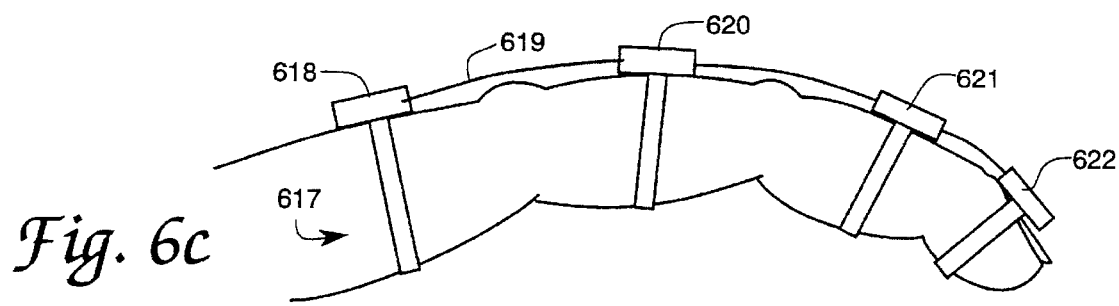
FIG. 6c is a side view of a finger showing a Goniometer method using linear potentiometers mounted on the digital segments.

FIG. 8b uses linear potentiometers with flexible actuators. Here, the changes in sensed length are transferred to orientation changes to the pneumatic actuator. This type of goniometer is further illustrated in FIGS. 6a and 6c. FIG. 6a is a side view of a finger mounted with rotational potentiometer goniometer apparatus. FIG. 6c is a goniometer method using linear potentiometers mounted on digital segments. In FIG. 6c, the displacement of the potentiometers correlates to the matatarsal angles. The angle desired is determined based on proportional changes in auto-inductance between the sensors.

Figure 6D:
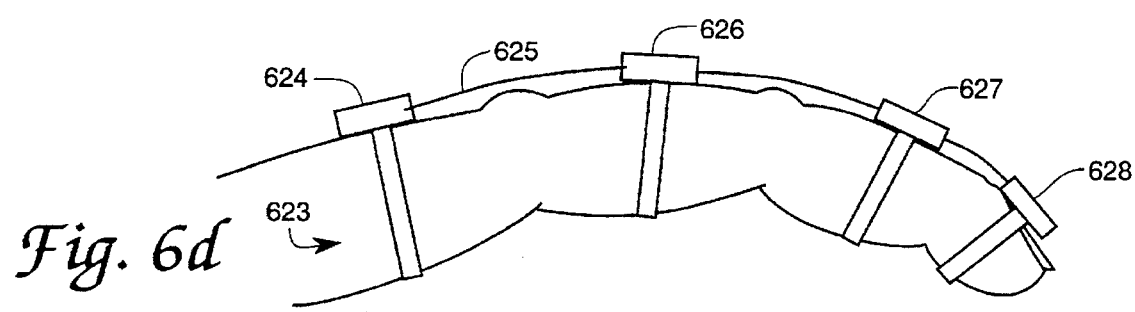
FIG. 6d is a side view of a finger showing a Goniometer method using force sensoring elements such as strain gauges, pressure sensors, etc.

In the second goniometer type, 618 correlates to the metatarsal phalangeal angle, the displacement of the second potentiometer 620 correlates to the proximal interphalangeal joint angle and displacement of the third potentiometer 621 correlates to the distal interphalangeal joint angle. The three distal potentiometers 620, 621 and 622 receive the flexible potentiometer rod 619 from the first potentiometer 618. Other goniometer arrangements include sensing elements such as strain gauges as illustrated in FIG. 6d or pressure sensors.

The human now has an active manner of inducing motion via his fingers. This gives feedback (via brain commands to the fingers of the patient) as well as control of the pneumatic actuators to control forces on the legs. It has been shown in the literature, in the article "Sensory Substitution Systems" studies [see referenced 2, 3, 4] that feedback of this nature which is anthropomorically similar will transfer with minimum interference.

Figure 9:
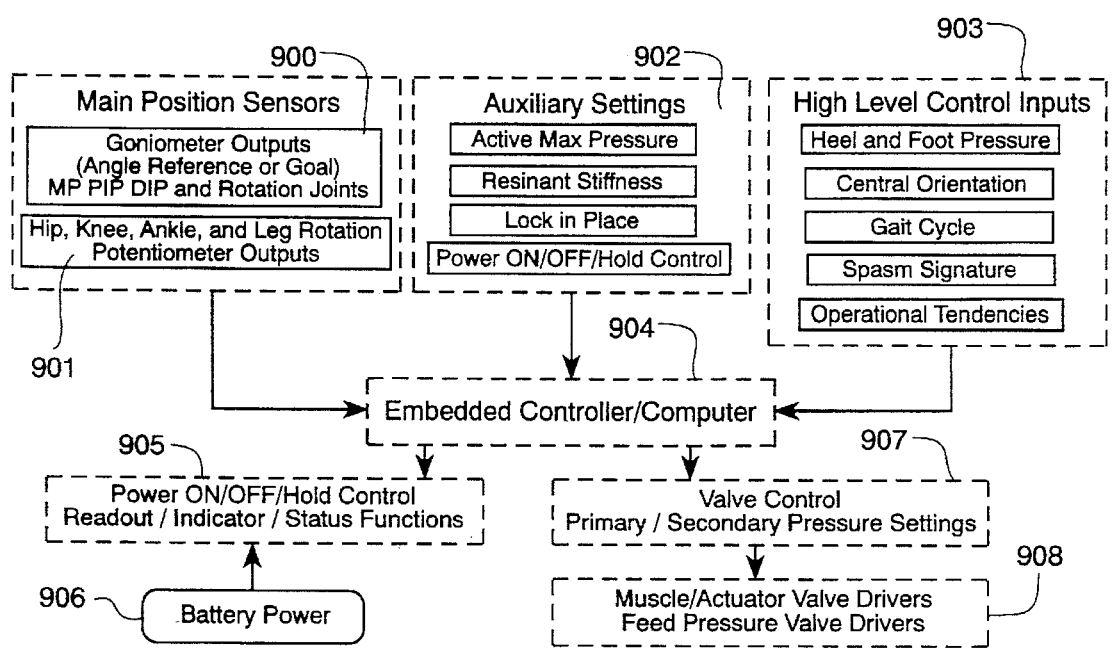
FIG. 9 is a block diagram of the control and actuation system.

It is worthwhile to now discuss algorithms that change the force characteristics and aid in the stability and operation of walking. One of the inputs to the controller 904 in FIG. 9 is the electrical signals 900 from the goniometers. This now changes the logic of the electronics. In this case, for example, one may map 1:1 signals from the fingers to the lower limb motion with a scaling constant. The electronic logic here (most likely of an analog nature) would first test to determine if the goniometer signals were to be used as inputs. Again, as before, the patient has manual control over the device. A manual controller console is shown at 1004 in FIG. 10. The console is secured by a strap-on guard around the driving hand. Also mounted on it are feed back LED's and status readouts. With the manual controller console, a patient can exclude or include specific inputs into the electronics control. The controller to the pneumatic actuator could output a force scaled by force units and angular units to see what factors would assist walking.

Referring to an exoskeleton structure of FIG. 7, three or more Velcro straps 706 may be attached to the leg at the upper thigh, the upper calf and near the ankle, respectively, to attach the device of the present invention to the leg. The hip segment 708 of the device is attached to a weight bearing lower torso harness 701. The back view 715 of the harness assembly shows cabling of the pneumatic actuators with the actuators mounted at 717. Length adjustment for the thigh and leg segments of the patients are shown at 702 and 703 respectively, as well as a hip width adjustment at 711. The foot plate 707 is shown mounted with force sensors for distributed force measurement and secured with shoe or foot straps 704.

FIG. 7 also shows hip socket motion in accordance with the present invention by actuating leg rotation about the central femur 709 within the upper thigh 718. The leg rotation joint 716 is a combination of hip joint and leg rotation and provides most of the hip mobility assist range of motion. The motion is provided by the pull-pull assembly 712 using one pneumatic actuator and an opposing spring similar to the mechanism shown and discussed in FIG. 3 below. The spring pulls the leg rotation back to a neutral rotation of 5–10 degrees distally pronated from straight forward for stability. The hip segment belt apparatus may be used for the sensors for the angle θ1, and an air reservoir and control device for the pneumatic actuator 10 of FIG. 1.

There are two sources of power required for the present invention:

(1) A small pneumatic source of compressed air to actually produce forces on the lower limbs and also to change the force actuated from a zero value to a non-zero value.

(2) An electric battery, illustrated at 906 in FIG. 9, is also required since the electronics required to perform the logic in controller 904 will require some power. It is recommended that the battery be rechargeable and last for a normal 6–10 hour activity day. Also, the transmission of the goniometer readings from the fingers to the pneumatic actuators is accomplished by wires on the orthosis frame.

DESCRIPTION OF APPARATUS

This device provides weight bearing and structural stability as well as assistive power to joints. This contributes to the total mobility enhancement of the wearer regardless of the mobility impairment. As a high-power mobility assist, the exoskeleton is capable of providing a normal person with additional strength and support, thereby creating a state of "super-mobility".

In the FIG. 1 active orthosis apparatus, the four segments of the patient's legs are each reinforced by braces which have actuators for the three joints. The collection of braces and joints form an exoskeleton which fits around one or both legs. The whole four segment apparatus may not be required in each use of the invention as a person may only have mobility impairment below the ankle, knee or upper thigh. All diagrams shown, therefore, include the total possible assembly of the MAPAS system, reduced editions are also possible. Angles Theta-n-L illustrated in FIG. 1a are those on the leg where n is any joint 1, 2, or 3. The exoskeleton brace can be made of plastic, fiberglass, or aluminum to suit the requirements of the user.

Variations in the described apparatus suit different requirements of support, strength, actuation, and weight. The basic configuration in FIG. 1 is embellished in examples of a light plastic molded version in FIG. 2a. FIG. 2a is a side view of a molded-brace type support having molded structural segments for the upper-thigh 202, lower-thigh 204, upper-leg 206 and lower-leg 208. There is also a molded shape hip brace element 200 and alternate joint designs are shown at 211, 212 and 213. A molded-brace type support is suggested for use with muscular dystrophy, multiple sclerosis and rehabilitation patients having low force, light load-bearing and lower energy requirements.

A more substantial heavy-duty version is shown in FIG. 2b. FIG. 2b is a side view of a metal brace having metal structural segments for the upper thigh 216, lower thigh 218, upper leg 221 and lower leg 223. The base 219 of the metal thigh segment contains the knee joint and the top 220 of the metal leg segment receives the knee joint and has random operating memory stop to prevent hyper-extension of the knee.

The pneumatic actuators employed in the present invention operate in pairs and allow for various force states, as shown in FIG. 1b by the opposed clockwise and counter-clockwise elements 111 and 112 which operate on the rotational joint 113 to provide torque achieved through attached lines looped cables or cables fed through guides on the cable radius 114 in. These actuators provide contractile forces about a joint 113 creating the torque required for mobility enhancement or stability.

Actuators used for this device can be pneumatic muscles, silicone tubing sheathed with a plastic mesh and capped at each end. Such a muscle arrangement in pull-pull form is shown in FIG. 3 of the drawings. In the FIG. 3a muscle pair the top muscle 300 is represented to be operating at a lesser pressure so as to create a smaller pulling force at the pulley 306 and the lower muscle 301 operating at a greater pressure so as to have an expanded body and shortened woven mesh 303a. Expansion of the woven mesh 303a has produced a contraction in the "or" muscle 301 to provide a pulling force at the pulley 306. The fixed and moveable muscle end caps 302 and 304 in FIG. 3 provide access to the pressurized air circuit via a port such as appears at 305. These "muscles" therefore have principles of operation, as shown in FIG. 3a, which in some respects emulates normal muscles. Since the silicon tubing 303 acts as a balloon, when inflated by applied air the tubing diameter increases and causes a contraction in the outer mesh 303a. Contraction of the mesh translates into contractile force and creates the pull-pull actuation of torque about the joint. Like real tissue muscles, only contractile forces can be produced by the FIG. 3a muscles. The benefit in using these muscles over standard air cylinders is a savings in weight and cost.

Figure 3B:
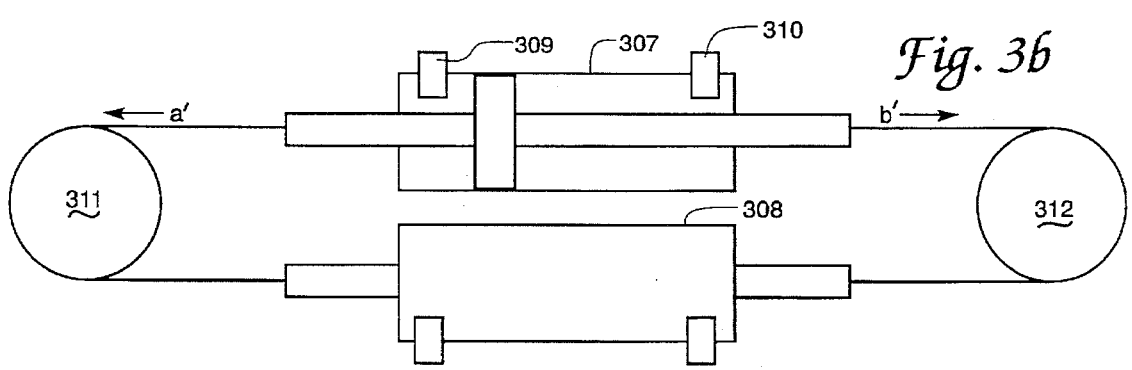
FIG. 3b is a diagram of a push-pull actuator using two double-ended cylindrical pneumatic actuators in a series.

Using standard double-acting air cylinders in a push-pull arrangement is also possible for embodying the invention as shown in FIG. 3b. The push-pull name for the FIG. 3b cylinders arises from the possible application of air pressure via the port 309 or the port 310 to the cylinders 307 and 308. Port 309 air application achieves movement in direction b' at the FIG. 3 joint rotation pulley 312 and structure mounted bore pulley 311. Alternatively, application of air pressure at the port 3 10 achieves movement in direction a' at these pulleys. Air applications to the oppositely disposed ports of cylinder 308 can be used to supplement the forces generated at pulleys 311 and 312.

Figure 3C:
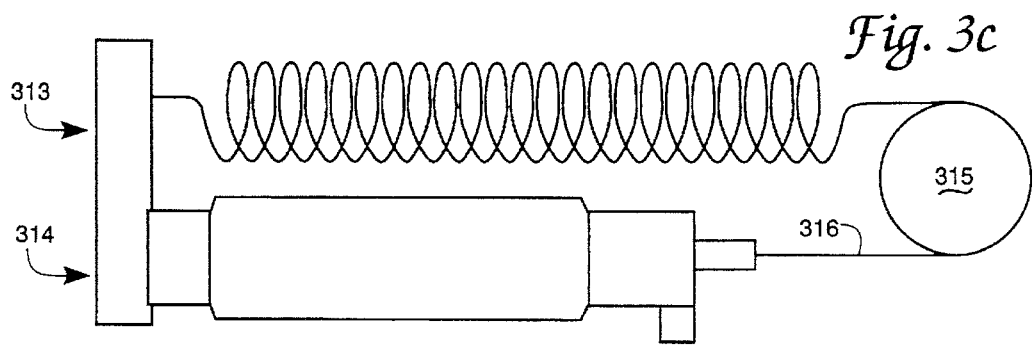
FIG. 3c is a diagram of a pull-pull actuator using a spring as a constant pulling force whereas the muscle would need to overcome the spring's force to actual clockwise motion (used in the leg twist above the hip and in toe-flexion about the ankle joint)

In the human ankle joint, the joint movement muscles achieve a large force in foot plantation movement (a force provided via the calf muscle), whereas foot reduction (or toe-lift) typically involves a lesser force. A spring can therefore be substituted for an opposing muscle in the case of such a lopsided torque requirement, such an arrangement is shown in the pull-pull actuator of FIG. 3c. In FIG. 3c a muscle of the type used at 301 in FIG. 3a appears at 314 where opposed or pressurized by the extended spring 313 which provides pulling force throughout cable 316 along the cable path involving joint and pulley 315.

Integration of manual goniometric inputs, control algorithms, joint and special sensors such as distributed foot-to-ground pressure make the active orthosis function as a true mobility assist. Control algorithms or circuitry which drive this exoskeleton may be simple analog devices or be more complex and require embedded computer algorithms depending on the requirement of the user. The most complex case occurs when the MAPAS device is applied to a spastic person with muscle and bone atrophy. Here, little support is provided from the legs, and any muscular activity is random and complicates coordinated motion. Control algorithms in this case preferably incorporate "spastic signatures" to aide in the control of coordinated walking, rising, climbing, or descending. Such signatures are represented in block 903 in FIG. 9. Generally, block 903 inputs to the controller serve as primary coordination systems for a high level controller algorithm based in the software of an embedded controller or operational computer. These spastic signatures may be programmed into an algorithm which expects random forces and compensates for them.

Figure 11:
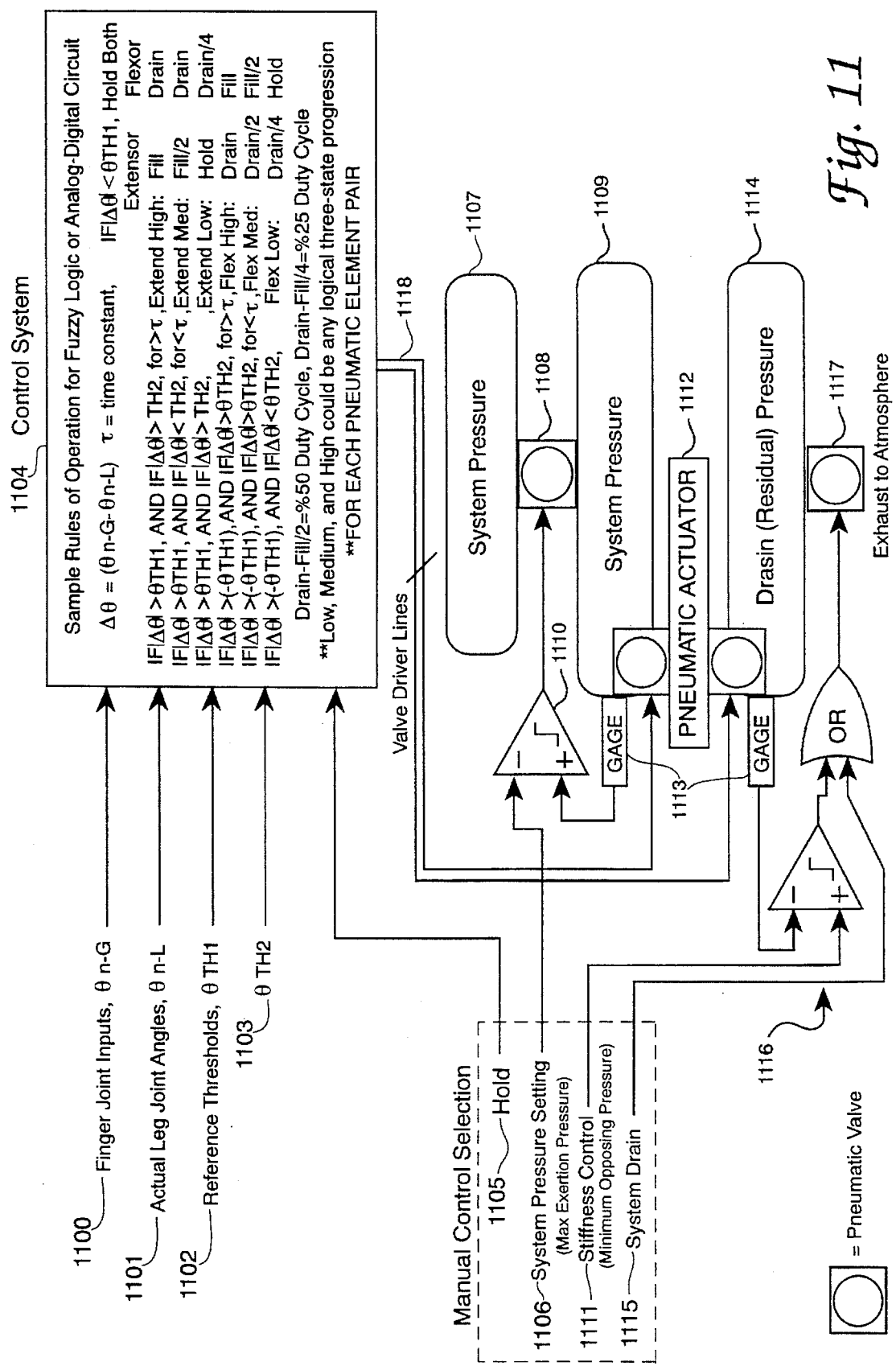
FIG. 11 is a diagram of MAPAS control system pathways showing incorporation of goniometric signals, a three-tiered pressure hierarchy, and a basic control method.

A control system for the invention, a system based in discrete electronic components is shown in FIG. 11. FIG. 11 shows the integration of the sensor and manual control inputs to control the MAPAS system. The manual control selection provides a "hold" function 1105 which is an input to the control algorithm that prevents any valves from being open and in turn no filling or draining of pneumatic elements occurs. The second manual control option 1106 is a system pressure function. System pressure 1107 is the maximum exertion pressure that a pneumatic element can have if it is entirely full. The supply pressure, typically a very high pressure, is tapped to refresh the lower pressure system pressure. If the system pressure is set from 30 PSI to 90 PSI, an appropriate supply pressure would be 500–2000 PSI. The level which the valves open to maintain is the system pressure threshold setting. Setting this pressure threshold high is appropriate for walking, running, stair climbing, etc. setting this pressure threshold low would be appropriate for sitting, laying, obtaining recreational range of motion, etc. The main valve 1108 allows high supply pressure to maintain the pressure minimum of the system pressure and the final system pathway valve 1117 exhausts to ambient air.

The third manual control is at 1111, the difference in pneumatic element pair's force, can be considered stiffness or tension. Controlling the minimum opposing pressure allows the user to set the amount of stiffness. Exhaust gas is drained from the pneumatic elements into a third tank, a residual tank. By not letting all of the air out of an opposing pneumatic element, stability is enhanced because there is a counter torque already in place. Higher stiffness decreases total output torque. The fourth manual control is system drain at 1115 which allows a manual input to drain to ambient air all residual pressure in all of the pneumatic elements. This could also be connected to the primary valve to drain the system pressure tank, and possibly the supply pressure tank.

For automatic control, the control algorithm, illustrated in block 1104, may be a set of fuzzy logic rules in an on-board computer, be part of a software control algorithm, or be built in simple analog/digital circuits based in simple logic gates and voltage comparators. In this example, the main control algorithm (1104) includes a set of operation rules. These rules describe a seven state output for each pneumatic actuator pair, consisting of the opposing flexor and extensor elements. The case of the ankle and hip rotation is not specifically described but since these two joints only have flexors, the algorithm would use only five states. The valves are digitally driven, as they have only three states themselves, fill, drain, and hold (no flow). To enhance the use of simple air valves, the inputs can be pulsed at a certain duty cycle to create middle stages such as "Fill/2" where for the period of fill time, the filling of the air occurs only 50 percent of the time. These operation rules are based on the capability of first comparison of levels, and no in between states other than those presented. With analog processing a PID controller (either analog or digital) could be written in place of this one. Also, an advanced computer software program incorporating spasm signatures, force feedback from the Velcro straps or distributed foot pressure, and other supplemental inputs may be used to control the system in a very high-level fashion.

MAPAS Operations Procedures

The operations and procedures of the Pneumatic legs will require skill in coordination, inherent safety measures and procedural safety measures to ensure proper operation. The inherent safety features include three lateral hinge joints per leg, a planated ankle support, a planated hip, a torso harness, balance stabilizers in the torso harness, and a high pressure air supply belt. Each joint is limited in rage of motion by compressible material. These inherent safety features will help the user function properly.

The procedures of operation are important to follow. Unwanted motions or failure to actuate proper motions will result if attention is not paid to the pressure regulation of the system. Three processes are outlined below to guide the user in their proper orchestration.

1) Powering-Up

To use the legs, a sufficiently high pressure air reserve must be present and the secondary (supply) tank (if used) must be set at an adequate pressure. Since the pressure regulators or valves shown at 1008 in FIG. 10 will be position actuating, the initial state of the supply pressure 1007 and finger controllers 1003 must be turned active under control to avoid instant uncontrolled high force motion. To do this, first set the supply pressure threshold to its lowest value and then activate the manual control circuitry 1002a. Once those two things are set, activate the supply pressure regulator (or main valve controller 1006) and slowly increase the supply pressure threshold to the desired amount.

2) Operation

Figure 10:
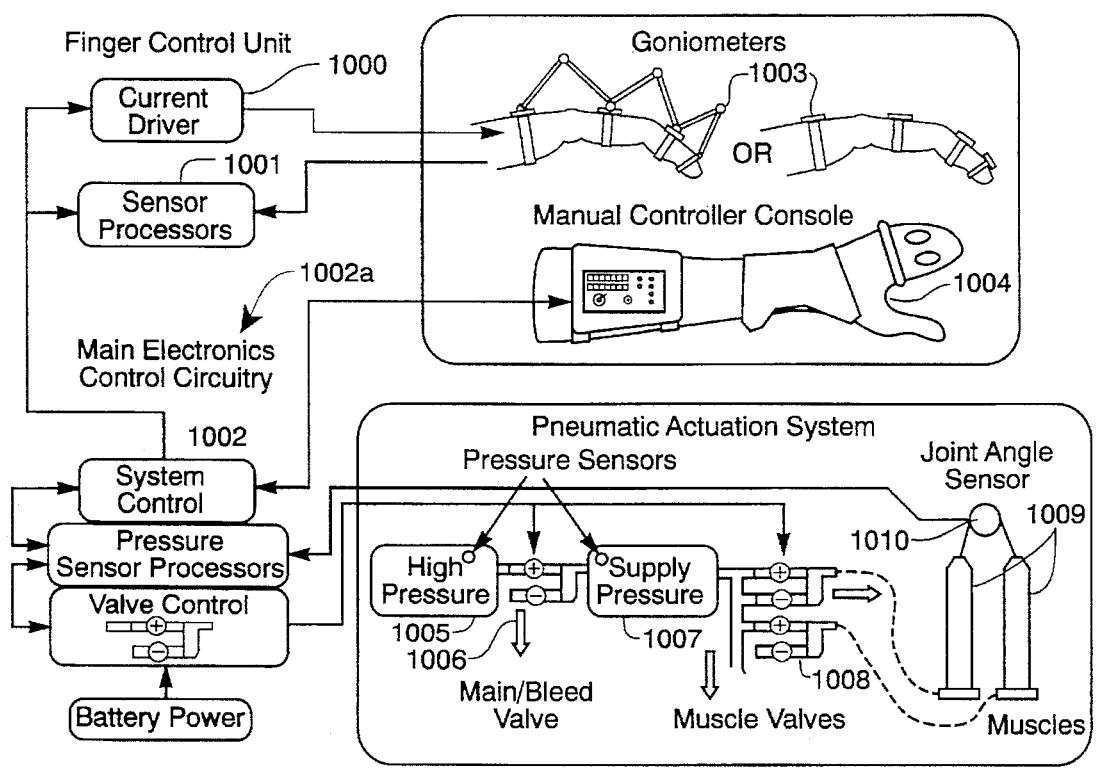
FIG. 10 is a diagram of MAPAS electrical system pathways, showing general components which are paths of critical signals.

With sufficient supply pressure at 1007 in FIG. 10, the legs illustrated at 1009 will function under position actuation. An air pressure difference will be enacted until the angle of the legs matches that of the individual finger input from the Manual Controller Console mounted on the wrist There are two buttons on the Manual Controller Console base, located under D-4 (ring finger), and under D-5 (pinkie finger). The embedded controller and or computer allows inputs from these buttons to control the MAPAS valve settings. It is possible to allow for progressive inputs to widen the input possibilities with only two buttons. A table of possible commands is listed here, each designed to aide in the total operation of the MAPAS in any form or application:

D-4 and D-5: Return leg control (release hold)
D-4 then D-4: Suspend leg control (hold force)
D-5 then D-4: Bleed Valve open/Main Valve closed (power down) D-5 then D-5: Reset conditions (Supply Pressure Regulation, Supply Pressure Threshold and Manual Controller Console active)

Three potentiometers are also mounted on the Manual Controller Console controller they actuate:

P-1: Left leg ambient stiffness set point
P-2: Right leg ambient stiffness set point
P-3: Misc. input to controller algorithm Typical adjustments of these potentiometers include the option to increase the level of use upon power up and modification to suit the environment (peak for strength requirements, medium for locomotion, lower for sitting/laying motions, and lowest for power up).

System activation switches are located on the primary circuit housings and are marked by LEDs on the housings and the MCC controller.

3) Powering Down

To turn the system off, changing the primary tank or recharging/changing batteries, a similar safety set of requirements are followed. First, decrease both the Supply Pressure Threshold set points to their lowest value a few minutes early to drain most of the supply air. Next, move to a neutral position, activate the "Hold Force" option (press D-4 then D-4), and then deactivate the Manual Controller Console finger control. Now no pressure should be sent to the legs but the supply pressure tank has residual air. This can be kept for emergencies even when the high pressure tank is not attached. For most safety concerns, drain the supply tank by opening the Bleed Valve and keeping the Main Valve closed (press D-5 then D-4). Replace the High Pressure Tank with the Main Valve closed (should be indicated by LEDs).

Goals for MAPAS Structural Development

1) Goals include developing an active exoskeleton frame which will be used to enhance/actuate locomotion of the wearer and enable relatively normal walking and other leg motions.

2) Features of MAPAS include
   a. Mounts easily with central lower torso harness and various straps in the harness and along the legs.
   b. Has joints which are relatively thin, strong, and will survive constant bending over time without decay.
   c. Provides the resting location of the Leg Abduction 12 degrees away from center.
   d. Provides Range of Motion for the various joints with small neoprene soft stops. The Range of Motion should be the same as the wearer and not restrict motion unless required by the user.

Advantages and New Features

The three main advantages of this device are:

(1) The nonlinear force and stabilization capability in extension and contraction provide ease to the patient in extending his leg when motion in this direction is required and stability when the leg contracts and supports weight in the reverse direction;

(2) The portability of the pneumatic gas sources and their type of actuation provides a means to have an active orthosis device to assist the patient in walking. This advantage distinguishes it from other devices which do not directly provide a patient ambulatory assistance; and (3) The unique process by which the patient drives the device by using his fingers in a manner anthropomorphically similar to the way the legs move, will expedite learning and the use of the device. The natural mapping of one body motion to coordinate another motion has been shown to be most successful.

It is understood that certain modifications to the invention as described may be made, as might occur to one with skill in the field of the invention, within the scope of the appended claims. Therefore, all embodiments contemplated hereunder which achieve the objects of the present invention have not been shown in complete detail. Other embodiments may be developed without departing from the scope of the appended claims.

What is claimed is:

1. An orthosis for assisting locomotion in a patient, said orthosis comprising:

a brace device, with means for attaching the brace device to a leg of said patient; actuator means coupled to the brace device;

goniometer means for sensing patient finger motion;

control means having input from the goniometer means and output to the actuator means;

wherein the control means is driven by the patient's fingers by signals from the goniometer means in an anthropomorphic manner similar to the leg motion, and the motion of fingers replicates motion that is desired for the legs to perform.

2. An orthosis for assisting locomotion in a patient, said orthosis comprising:

a brace device including an upper leg member, a lower leg member, a foot plate, a knee joint which is attached to the upper and lower leg members, and an ankle joint which is attached to the lower leg member and to the foot plate, with means for attaching the brace device to a leg of said patient;

sensing means including sensors coupled to said brace device;

actuator means coupled to the upper and lower leg members and including a portable pneumatic gas source and goniometer means attachable to fingers of said patient for actuating orthosis muscles in an anthropomorphic manner similar to leg motion, the motion of fingers replicating desired leg motion; and control means having input from said sensing means and output to said actuator means, position and strength of said orthosis muscles being adaptively responsive to said sensing means input to said control means including force or operating characteristics of legs of said patient to selectively provide extended, contracted or stable leg positions.

* * * * *